US009719891B2

(12) United States Patent
Blackmon et al.

(10) Patent No.: US 9,719,891 B2
(45) Date of Patent: Aug. 1, 2017

(54) SIMULTANEOUS MULTI-POINT TESTING SYSTEMS AND METHODS

(71) Applicant: The Southern Company, Atlanta, GA (US)

(72) Inventors: Gary Blackmon, Atlanta, GA (US); Mitchell Gober, Douglasville, GA (US)

(73) Assignee: The Southern Company, Atlanta, GA (US)

( * ) Notice: Subject to any disclaimer, the term of this patent is extended or adjusted under 35 U.S.C. 154(b) by 0 days.

(21) Appl. No.: 14/710,938

(22) Filed: May 13, 2015

(65) Prior Publication Data

US 2016/0334310 A1    Nov. 17, 2016

(51) Int. Cl.
*G01N 1/26* (2006.01)
*G01N 33/00* (2006.01)

(52) U.S. Cl.
CPC ............. *G01N 1/26* (2013.01); *G01N 33/004* (2013.01); *G01N 33/0036* (2013.01); *G01N 33/0037* (2013.01)

(58) Field of Classification Search
CPC ....................................................... G01N 1/26
See application file for complete search history.

(56) References Cited

U.S. PATENT DOCUMENTS

| | | |
|---|---|---|
| 3,842,678 A | 10/1974 | De Baun et al. |
| 4,414,858 A | 11/1983 | Peterson et al. |
| 4,442,720 A | 4/1984 | Apley et al. |
| 4,856,352 A * | 8/1989 | Daum .................. G01N 1/2247 73/1.06 |
| 6,094,968 A | 8/2000 | Scheufler et al. |
| 6,615,679 B1 | 9/2003 | Knollenberg et al. |
| 6,904,815 B2 | 6/2005 | Widmer |
| 6,976,397 B2 | 12/2005 | Widmer |
| 7,096,750 B2 | 8/2006 | Kreck et al. |
| 7,340,939 B2 | 3/2008 | Jansen |
| 8,347,701 B2 | 1/2013 | Stedman |
| 2010/0064951 A1 | 3/2010 | Storm et al. |
| 2014/0033796 A1 | 2/2014 | Stedman |
| 2014/0251031 A1 | 9/2014 | Kumagai |

* cited by examiner

*Primary Examiner* — Paul Hyun
(74) *Attorney, Agent, or Firm* — Troutman Sanders, LLP; Ryan A. Schneider; Dustin B. Weeks

(57) ABSTRACT

An exemplary embodiment of the present invention provides a simultaneous multipoint testing system for analyzing the composition of a fluid in a duct. The system can comprise a plurality of probes each having a plurality of sample legs at different locations within the duct. Each probe can also comprise a mixing chamber for mixing fluid samples collected by each of the sample legs. The system can further comprise a global mixing chamber configured to receive the mixtures of fluid samples from each probe mixing chamber and mix those fluid samples to create a global fluid sample. The system can further comprise an analyzer configured to receive at least a portion of the global fluid sample and measure levels predetermined compounds present in the at least a portion of the global fluid sample.

8 Claims, 2 Drawing Sheets

SIMULTANEOUS MULTI-POINT TESTING SYSTEMS AND METHODS

TECHNICAL FIELD OF THE INVENTION

The various embodiments of the present disclosure relate generally to testing systems and methods. More particularly, the various embodiments of the present invention are directed to system and methods for simultaneously testing the composition of a fluid sampled at multiple locations.

BACKGROUND OF THE INVENTION

Electric power generation plants commonly burn some type of fossil fuel, e.g., natural gas, coal, fuel oil, etc., during the production of electricity. The flue gas resulting from the combustion of these fuel sources contains several compounds, including, but not limited to, nitrous oxides ("NOX"), carbon monoxide ("CO"), carbon dioxide ("CO2"), and oxygen ("O2"). It is important for operators to closely monitor the levels of these compounds in the flue gas stream to determine whether certain operating conditions should be changed. Accordingly, conventional systems exist that allow a sample to be taken from the flue gas stream and analyzed to determine the levels of certain compounds present in the gas. To ensure an accurate analysis of the flue gas as a whole, however, it is important to take samples from multiple points in the duct in which the flue gas is traveling because the detected levels can vary from point to point. By taking the readings from multiple locations in the duct, the operators can use statistical calculations, e.g., taking the average (possibly after excluding data point outliers, to obtain a clearer picture of the actual levels of compounds being emitted from the plant.

These conventional systems, however, operate in one of two ways. First, each system can use a probe at each location from which a data point will be taken to obtain a flue gas sample from that location. A sample from a first location can then be sent to a analyzer that measures the levels of certain compounds in the sample (e.g., as a percentage of the total sample size). Then, a sample from the next location is sent to the analyzer for detection of compound levels. This process is continually repeated by oscillating through each of the probes. Unfortunately, these samples cannot simultaneously monitor the levels at each probe location; rather, only one sample at a time from each location can be sent to the analyzer. The second types of systems can allow for simultaneous monitoring of levels at each probe, but require a separate analyzer to continually monitor each location, which leads to increases costs both from an equipment standpoint (e.g., multiple analyzers) and from a labor standpoint (e.g., labor for continually calibrating each of the analyzers).

Therefore, there is a desire for systems and methods that allow for the simultaneous testing of multiple samples from different locations in a more economical manner. Various embodiments of the present invention address these desires.

BRIEF SUMMARY OF THE INVENTION

The present invention relates to multipoint testing systems and methods. An exemplary embodiment of the present invention provides a simultaneous multipoint testing system for analyzing the composition of a fluid in a duct. The system can comprise a first probe, a second probe, a global mixing chamber, and an analyzer. Each of the first and second probes can comprise a first sample leg, a second sample leg, a probe mixing chamber and an output. The first sample leg can be in fluid communication with a first location within the duct and configured to receive a first fluid sample from the duct. The second sample leg can be in fluid communication with a second location within the duct and configured to receive a second fluid sample from the duct. The probe mixing chamber can be in fluid communication with the first and second sample legs and can be configured to receive the first and second fluid samples and generate a probe fluid sample comprising a mixture of the first and second fluid samples. The output can be in fluid communication with the probe mixing chamber and configured to output the probe fluid sample. The global mixing chamber can be in fluid communication with the outputs of the first and second probes and configured to receive the probe fluid samples from the first and second probes and generate a global fluid sample comprising a mixture of the probe fluid samples from the first and second probes. The analyzer can be configured to receive at least a portion of the global fluid sample and measure levels predetermined compounds present in the at least a portion of the global fluid sample.

In some embodiments, the system can further comprise a vacuum pump in fluid communication with the global mixing chamber and the first and second probes. The vacuum pump can be configured to induce a negative pressure within the first probe and the global mixing chamber with respect to the duct so that fluid samples are pulled from the duct, through the first and second probes, and through the mixing chamber.

In some embodiments, the duct can be an exhaust duct of an electric power generation plant and the fluid in the duct can be a flue gas.

In some embodiments, the predetermined compounds can comprise one or more nitrous oxides, carbon monoxide, carbon dioxide, and oxygen.

In some embodiments, a flow rate of fluid through each of the first and second legs of the first and second probes can be within 10% of an average flow rate of fluid through the first and second legs of the first and second probes.

In some embodiments, the system can further comprise a calibration system comprising a calibration fluid source that can be configured to provide a calibration fluid to the probe mixing chambers of the first and second probes at a pressure sufficient to prevent the fluid in the duct from entering the first and second probes. The calibration fluid can comprise known levels of the predetermined compounds.

Another exemplary embodiment of the present invention provides a method of simultaneously testing levels of predetermine compounds in a fluid at multiple points in a duct. The method can comprise obtaining a plurality of fluid samples, each fluid sample being obtained from a different location in the duct, transferring a first portion of the plurality of fluid samples to a first mixing chamber, mixing the first portion of the plurality of fluid samples in the first mixing chamber to generate a first mixed fluid sample, transferring a second portion of the plurality of fluid samples to a second mixing chamber, mixing the second portion of the plurality of fluid samples in the second mixing chamber to generate a second mixed fluid sample, transferring the first and second mixed fluid samples to a third mixing chamber, mixing the first and second mixed fluid samples in the third mixing chamber to generate a global fluid sample, and measuring the levels of the predetermined compounds in the global fluid sample.

In some embodiments, the method further comprises inducing a negative pressure within the first, second, and third mixing chambers relative to the duct to transport fluid from the duct, through the first, second, and third mixing chambers.

In some embodiments, the duct can be an exhaust duct of an electric power generation plant and the fluid in the duct can be a flue gas.

In some embodiments, the predetermined compounds can comprise one or more nitrous oxides, carbon monoxide, carbon dioxide, and oxygen.

In some embodiments, a flow rate of fluid into each of the first and second mixing chambers can be within 10% of an average flow rate of fluid into the first and second mixing chambers.

In some embodiments, the method can further comprise performing a calibration step. The calibration step can comprise temporarily halting the flow of fluid from the duct into the first and second mixing chambers, transferring a calibration fluid from a calibration source to the first and second mixing chambers, transferring calibration fluid from the first and second mixing chambers to the third mixing chamber, and measuring the levels of the predetermined compounds in a sample of the calibration fluid. The calibration fluid can comprise known levels of the predetermined compounds.

Another embodiment of the present invention comprises a simultaneous multipoint testing system for analyzing the composition of a flue gas in a duct. The system can comprise a first probe, a second probe, a third probe, a fourth probe, a global mixing chamber, and an analyzer. The first probe can comprise a first sample leg, a second sample leg, a third sample leg, a first probe mixing chamber, and a first output. The first sample leg can be in fluid communication with a first location within the duct and configured to receive a first fluid sample from the duct. The second sample leg can be in fluid communication with a second location within the duct and configured to receive a second fluid sample from the duct. The third sample leg can be in fluid communication with a third location within the duct and configured to receive a third fluid sample from the duct. The first probe mixing chamber can be in fluid communication with the first, second, and third sample legs. The first probe mixing chamber can be configured to receive the first, second, and third fluid samples and generate a first probe fluid sample comprising a mixture of the first, second, and third fluid samples. The first output can be in fluid communication with the first probe mixing chamber and configured to output the first probe fluid sample. The second probe can comprise a fourth sample leg, a fifth sample leg, a sixth sample leg, a second probe mixing chamber, and a second output. The fourth sample leg can be in fluid communication with a fourth location within the duct and configured to receive a fourth fluid sample from the duct. The fifth sample leg can be in fluid communication with a fifth location within the duct and configured to receive a fifth fluid sample from the duct. The sixth sample leg can be in fluid communication with a sixth location within the duct and configured to receive a sixth fluid sample from the duct. The second probe mixing chamber can be in fluid communication with the fourth, fifth, and sixth sample legs. The second probe mixing chamber can be configured to receive the fourth, fifth, and sixth fluid samples and generate a second probe fluid sample comprising a mixture of the fourth, fifth, and sixth fluid samples. The second output can be in fluid communication with the second probe mixing chamber and configured to output the second probe fluid sample. The third probe can comprise a seventh sample leg, an eighth sample leg, a ninth sample leg, a third probe mixing chamber, and a third output.

The seventh sample leg can be in fluid communication with a seventh location within the duct and configured to receive a seventh fluid sample from the duct. The eighth sample leg can be in fluid communication with an eighth location within the duct and configured to receive an eighth fluid sample from the duct. The ninth sample leg can be in fluid communication with a ninth location within the duct and configured to receive a ninth fluid sample from the duct. The third probe mixing chamber can be in fluid communication with the seventh, eighth, and ninth sample legs. The third probe mixing chamber can be configured to receive the seventh, eighth, and ninth fluid samples and generate a third probe fluid sample comprising a mixture of the seventh, eighth, and ninth fluid samples. The third output can be in fluid communication with the third probe mixing chamber and configured to output the third probe fluid sample. The fourth probe can comprise a tenth sample leg, an eleventh sample leg, a twelfth sample leg, a fourth probe mixing chamber, and a fourth output. The tenth sample leg can be in fluid communication with a tenth location within the duct and configured to receive a tenth fluid sample from the duct. The eleventh sample leg can be in fluid communication with an eleventh location within the duct and configured to receive an eleventh fluid sample from the duct. The twelfth sample leg can be in fluid communication with a twelfth location within the duct and configured to receive a twelfth fluid sample from the duct. The fourth probe mixing chamber can be in fluid communication with the tenth, eleventh, and twelfth sample legs. The fourth probe mixing chamber can be configured to receive the tenth, eleventh, and twelfth fluid samples and generate a fourth probe fluid sample comprising a mixture of the tenth, eleventh, and twelfth fluid samples. The fourth output can be in fluid communication with the fourth probe mixing chamber and configured to output the fourth probe fluid sample. The global mixing chamber can be in fluid communication with the first, second, third, and fourth outputs and can be configured to receive the first, second, third, and fourth probe fluid samples and generate a global fluid sample comprising a mixture of the first, second, third, and fourth probe fluid samples. The analyzer can be configured to receive at least a portion of the global fluid sample and measure levels of predetermined compounds present in the at least a portion of the global fluid sample.

These and other aspects of the present invention are described in the Detailed Description of the Invention below and the accompanying figures. Other aspects and features of embodiments of the present invention will become apparent to those of ordinary skill in the art upon reviewing the following description of specific, exemplary embodiments of the present invention in concert with the figures. While features of the present invention may be discussed relative to certain embodiments and figures, all embodiments of the present invention can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present invention.

BRIEF DESCRIPTION OF THE DRAWINGS

The following Detailed Description of the Invention is better understood when read in conjunction with the appended drawings. For the purposes of illustration, there is shown in the drawings exemplary embodiments, but the subject matter is not limited to the specific elements and instrumentalities disclosed.

DETAILED DESCRIPTION OF THE INVENTION

To facilitate an understanding of the principles and features of the present invention, various illustrative embodiments are explained below. The components, steps, and materials described hereinafter as making up various elements of the invention are intended to be illustrative and not restrictive. Many suitable components, steps, and materials that would perform the same or similar functions as the components, steps, and materials described herein are intended to be embraced within the scope of the invention. Such other components, steps, and materials not described herein can include, but are not limited to, similar components or steps that are developed after development of the invention.

As discussed above, various embodiments of the present invention provide the ability to overcome the disadvantages of the prior art. Specifically, various embodiments of the present invention are capable of simultaneously testing fluid samples from multiple locations within a duct. Additionally, various embodiments of the present invention allow for such simultaneous multipoint testing without the need for separate analyzers for each location. While some embodiments of the present invention can be applied to electric power generation plants, particularly those using a fossil fuel as an energy source, those skilled in the art would understand that the present invention is not so limited. Rather, as persons of ordinary skill in the art would appreciate, various embodiments of the present invention can find applications in many systems where it is desirable to obtain a more complete and accurate understanding of the composition of a fluid in a fluid source.

Figure 1:
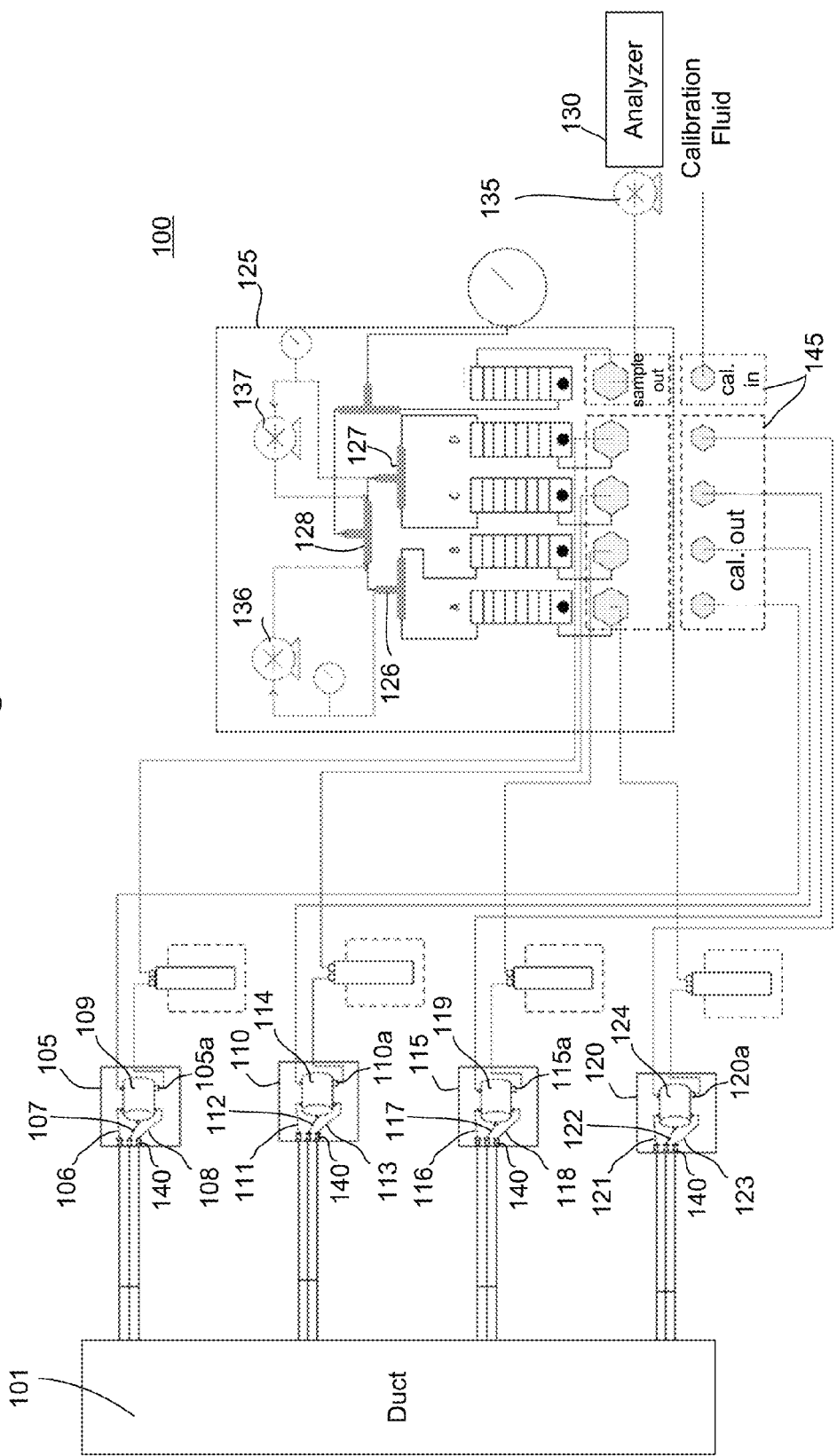
FIG. 1 provides a line diagram of a simultaneous multi-point testing system, in accordance with an exemplary embodiment of the present invention.
Figure 2:
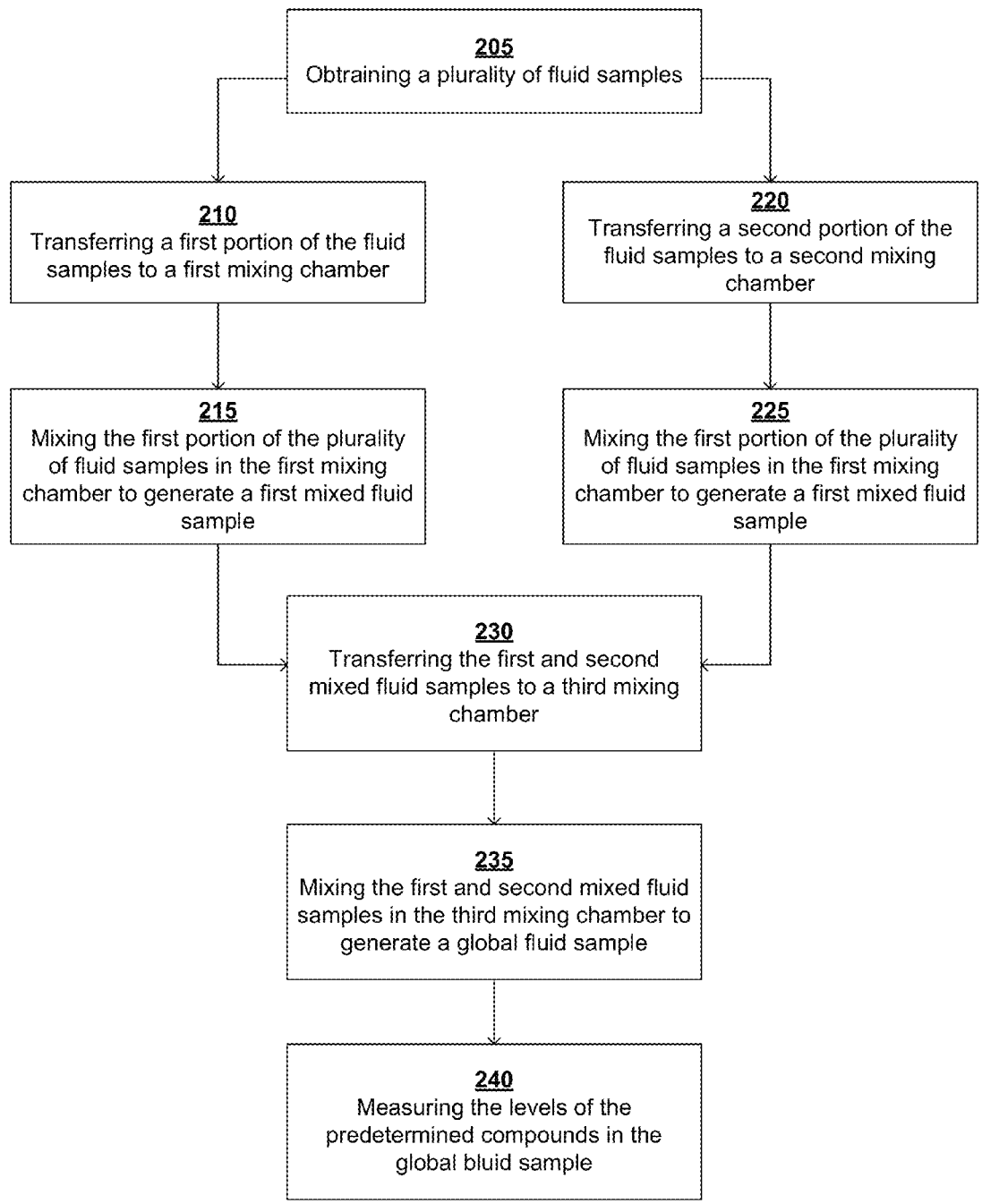
FIG. 2 provides flow diagram of a simultaneous multi-point testing method, in accordance with an exemplary embodiment of the present invention.

As shown in FIG. 1, an exemplary embodiment of the present invention provides a simultaneous multipoint testing system 100 for analyzing the composition of a fluid in a duct. The system can comprise multiple probes 105, 110, 115, and 120, a global mixing chamber 125, and an analyzer 130. While the system shown in FIG. 1 comprises four probes, various embodiments of the present invention can have any number of probes. For example, in some embodiments, the system comprises two probes. In some embodiments, the system comprises three probes. In some embodiments, the system comprises 10 probes. Each probe comprises a plurality of sample legs, e.g., 106, 107, 108, 111, 112, 113, 116, 117, 118, 121, 122, 123.

Each sample leg can be in fluid communication with a different location within the duct and can be configured to receive a fluid sample from the duct. The sample legs of each probe can also be in fluid communication with a probe mixing chamber, e.g., 109, 114, 119, 124, of the probes, such that a fluid sample can pass from the duct, through the sample leg, and into the probe mixing chamber. The probe mixing chamber, e.g., 109, can be configured to receive a fluid sample from each of the sample legs of the probe and mix the fluid samples to generate a probe fluid sample. The probe mixing chambers can be many different mixing chambers known in the art. In some embodiments of the present invention, the mixing chamber can comprise a hollow volume with multiple inputs and an output. The fluid samples from each leg can be received at the inputs. The turbulence created by the entry of all of the samples at the hollow volume can cause the samples to mix together to generate the probe fluid sample.

While the system shown in FIG. 1 comprises three sample legs for each probe, various embodiments of the present invention can have any number of sample legs for each probe. For example, in some embodiments, the system comprises two sample legs for each probe. In some embodiments, the system comprises four sample legs for each probe. In some embodiments, the system comprises 10 sample legs for each probe. Additionally, it is not required that each probe have the same number of sample legs. For example, a first probe could comprise two sample legs, while a second probe comprises five sample legs.

Each probe 105, 110, 115, and 120 can comprise corresponding output 105a, 110a, 115a, and 120a configured to deliver the probe fluid samples to the global mixing chamber 125. The global mixing chamber 125 receives the probe fluid samples and mixes the samples to generate a global fluid sample. The global fluid sample then is a mixture of each of the fluid samples from each of the sample legs of the probes, such that it provides an accurate sample of the fluid traveling through the duct. The global mixing chamber can be many different mixing chambers known in the art. In some embodiments of the present invention, the mixing chamber can comprise a hollow volume with multiple inputs and an output. The probe fluid samples from each probe can be received at the inputs. The turbulence created by the entry of all of the samples at the hollow volume can cause the samples to mix together to generate the global fluid sample. In some embodiments, the global mixing chamber 125 can comprise multiple stages. For example, a first probe fluid sample and a second probe fluid sample be mixed in a first sub-chamber 126 and a third probe fluid sample and a fourth probe fluid sample can be mixed in a second sub-chamber 127 at a first stage, and the mixtures in the first and second sub-chambers can be combined and mixed in a third sub-chamber 128 at a second stage. In this example, the mixture created in the third sub-chamber could be the global fluid sample for testing.

The analyzer can be configured to receive at least a portion of the global fluid sample and measure the levels of certain compounds, e.g., NOX, CO, $CO_2$, and $O_2$, within the fluid sample. The portion of the global sample fluid not sent to the analyzer can be vented. The analyzer can be many different analyzers known in the art. In some embodiments, the analyzer can comprise multiple analyzers, wherein each analyzer can measure the level of a specific compound within the sample (i.e., a first analyzer to measure NOX, and a second analyzer to measure CO). Thus, the system allows an operator to determine the composition of the fluid moving through the duct.

As also shown in FIG. 1, in some embodiments, the system can further comprise a vacuum pump 135 in fluid communication with the global mixing chamber 125 and the probes 105, 110, 115, and 120. The vacuum pump 135 can be configured to induce a negative pressure within the probes 105, 110, 115, and 120 (or mixing chambers and sample legs of the probes) and the global mixing chamber 125 with respect to the duct 101 so that fluid samples are pulled from the duct 101, through the sample legs, probe mixing chambers 109, 114, 119, and 124, and global mixing chamber 125. In some embodiments, additional pumps 136 and 137 can be used to assist in moving the fluids through the various components of the system 100. For example, as shown in FIG. 1, a pump 136 can be placed between the first sub-chamber 126 and the third sub-chambers 128 and pump can be placed between the second sub-chamber 127 and the third sub-chamber 128.

In some embodiments, the duct can be an exhaust duct of an electric power generation plant and the fluid in the duct can be a flue gas. In some embodiments, the predetermined compounds can comprise one or more nitrous oxides, carbon monoxide, carbon dioxide, and oxygen. As those skilled in the art would understand, however, various embodiments of the present invention can be used to measure the levels of many different compounds known in the art.

It can be important in some embodiments to ensure that the global fluid sample is an accurate representation of the fluid flowing through the duct. This can be more likely when the amount of fluid collected at each sample leg is substantially equal. Accordingly, some embodiments of the present invention seek to ensure that the flow rates through each of the sample legs are about the same. For example, in some embodiments, a flow rate of fluid through each of the first and second legs of the first and second probes can be within 10% of an average flow rate of fluid through the first and second legs of the first and second probes. The flow rates through each sample leg can be controlled many different ways known in the art. For example, in some embodiments, the size of a critical orifice 140 at the sample leg can be adjusted to control the flow rate of the sample fluid through that sample leg.

In some embodiments of the present invention, it may be important to calibrate the system from time to time to ensure accuracy of results obtained. Accordingly, in some embodiments, the system can further comprise a calibration system comprising a calibration fluid source 145, e.g., a pump in communication with a container of calibration fluid, configured to provide a calibration fluid to the probe mixing chambers of the first and second probes. The calibration fluid can be provided at a pressure sufficient to temporarily halt fluid in the duct from entering the probes. For example, while the pressure within the probe can be at a negative pressure with respect to the duct during normal operation, during the calibration process, the calibration fluid can be provided at sufficient pressure/volume/rate to induce a positive pressure in the probes, thus preventing fluid in the duct from entering the probes. The calibration fluid can comprise known levels of the predetermined compounds. Thus, the calibration fluid flows into the probe mixing chambers, then to the global mixing chamber and to the analyzer. The analyzer then measures the levels of compounds where a comparison can be made to the known levels of the calibration fluid.

Another exemplary embodiment of the present invention provides a method of simultaneously testing levels of predetermine compounds in a fluid at multiple points in a duct. The method can comprise obtaining a plurality of fluid samples 205, each fluid sample being obtained from a different location in the duct, transferring a first portion of the plurality of fluid samples to a first mixing chamber 210, mixing the first portion of the plurality of fluid samples in the first mixing chamber to generate a first mixed fluid sample 215, transferring a second portion of the plurality of fluid samples to a second mixing chamber 220, mixing the second portion of the plurality of fluid samples in the second mixing chamber to generate a second mixed fluid sample 225, transferring the first and second mixed fluid samples to a third mixing chamber 230, mixing the first and second mixed fluid samples in the third mixing chamber to generate a global fluid sample 235, and measuring the levels of the predetermined compounds in the global fluid sample 240.

In some embodiments, the method further comprises inducing a negative pressure within the first, second, and third mixing chambers relative to the duct to transport fluid from the duct, through the first, second, and third mixing chambers.

In some embodiments, the method can further comprise performing a calibration step. The calibration step can comprise temporarily halting the flow of fluid from the duct into the first and second mixing chambers, transferring a calibration fluid from a calibration source to the first and second mixing chambers, transferring calibration fluid from the first and second mixing chambers to the third mixing chamber, and measuring the levels of the predetermined compounds in a sample of the calibration fluid. The calibration fluid can comprise known levels of the predetermined compounds.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

What is claimed is:

1. A simultaneous multipoint testing system for analyzing the composition of a fluid in a duct, the system comprising:
  a first probe and a second probe, each of the first and second probes comprising:
    a first sample leg in fluid communication with a first location within the duct and configured to receive a first fluid sample from the duct;
    a second sample leg in fluid communication with a second location within the duct and configured to receive a second fluid sample from the duct;
    a probe mixing chamber in fluid communication with the first and second sample legs, the probe mixing chamber configured to receive the first and second fluid samples and generate a probe fluid sample comprising a mixture of the first and second fluid samples;

and an output in fluid communication with the probe mixing chamber and configured to output the probe fluid sample;

a global mixing chamber in fluid communication with the outputs of the first and second probes and configured to receive the probe fluid samples from the first and second probes and generate a global fluid sample comprising a mixture of the probe fluid samples from the first and second probes;

an analyzer configured to receive at least a portion of the global fluid sample and measure levels of predetermined compounds present in the at least a portion of the global fluid sample, and a calibration system comprising a calibration fluid source configured to provide a calibration fluid directly to the probe mixing chambers of the first and second probes, such that the calibration fluid is provided to the probe mixing chambers of the first and second probes without first passing through the duct, the calibration fluid provided at a pressure sufficient to prevent fluid from the duct from entering the first and second probes, the calibration fluid comprising known levels of the predetermined compounds.

2. The simultaneous multipoint testing system of claim 1, further comprising a vacuum pump in fluid communication with the global mixing chamber and the first and second probes, the vacuum pump configured to induce a negative pressure within the first probe and the global mixing chamber with respect to the duct so that fluid samples are pulled from the duct, through the first and second probes, and through the global mixing chamber.

3. The simultaneous multipoint testing system of claim 1, wherein the duct is an exhaust duct of an electric power generation plant and the fluid in the duct is a flue gas.

4. The simultaneous multipoint testing system of claim 1, wherein the predetermined compounds comprise one or more nitrous oxides, carbon monoxide, and oxygen.

5. A simultaneous multipoint testing system for analyzing the composition of a flue gas in a duct, the system comprising:
    a first probe comprising:
        a first sample leg in fluid communication with a first location within the duct and configured to receive a first fluid sample from the duct;
        a second sample leg in fluid communication with a second location within the duct and configured to receive a second fluid sample from the duct;
        a third sample leg in fluid communication with a third location within the duct and configured to receive a third fluid sample from the duct;
        a first probe mixing chamber in fluid communication with the first, second, and third sample legs, the probe mixing chamber configured to receive the first, second, and third fluid samples and generate a first probe fluid sample comprising a mixture of the first, second, and third fluid samples;
        and a first output in fluid communication with the first probe mixing chamber and configured to output the first probe fluid sample;
    a second probe comprising:
        a fourth sample leg in fluid communication with a fourth location within the duct and configured to receive a fourth fluid sample from the duct;
        a fifth sample leg in fluid communication with a fifth location within the duct and configured to receive a fifth fluid sample from the duct;
        a sixth sample leg in fluid communication with a sixth location within the duct and configured to receive a sixth fluid sample from the duct;
        a second probe mixing chamber in fluid communication with the fourth, fifth, and sixth sample legs, the probe mixing chamber configured to receive the fourth, fifth, and sixth fluid samples and generate a second probe fluid sample comprising a mixture of the fourth, fifth, and sixth fluid samples;
        and a second output in fluid communication with the second probe mixing chamber and configured to output the second probe fluid sample;
    a third probe comprising:
        a seventh sample leg in fluid communication with a seventh location within the duct and configured to receive a seventh fluid sample from the duct;
        an eighth sample leg in fluid communication with an eighth location within the duct and configured to receive an eighth fluid sample from the duct;
        a ninth sample leg in fluid communication with a ninth location within the duct and configured to receive a ninth fluid sample from the duct;
        a third probe mixing chamber in fluid communication with the seventh, eighth, and ninth sample legs, the probe mixing chamber configured to receive the seventh, eighth, and ninth fluid samples and generate a third probe fluid sample comprising a mixture of the seventh, eighth, and ninth fluid samples;
        and a third output in fluid communication with the third probe mixing chamber and configured to output the third probe fluid sample;
    a fourth probe comprising:
        a tenth sample leg in fluid communication with a tenth location within the duct and configured to receive a tenth fluid sample from the duct;
        a eleventh sample leg in fluid communication with a eleventh location within the duct and configured to receive a eleventh fluid sample from the duct;
        a twelfth sample leg in fluid communication with a twelfth location within the duct and configured to receive a twelfth fluid sample from the duct;
        a fourth probe mixing chamber in fluid communication with the tenth, eleventh, and twelfth sample legs, the probe mixing chamber configured to receive the tenth, eleventh, and twelfth fluid samples and generate a fourth probe fluid sample comprising a mixture of the tenth, eleventh, and twelfth fluid samples;
        and a fourth output in fluid communication with the fourth probe mixing chamber and configured to output the fourth probe fluid sample;
    a global mixing chamber in fluid communication with the first, second, third, and fourth outputs and configured to receive the first, second, third, and fourth probe fluid samples and generate a global fluid sample comprising a mixture of the first, second, third, and fourth probe fluid samples;
    an analyzer configured to receive at least a portion of the global fluid sample and measure levels of predetermined compounds present in the at least a portion of the global fluid sample, and
    a calibration system comprising a calibration fluid source configured to provide a calibration fluid directly to the probe mixing chambers of the first, second, third, and fourth probes, such that the calibration fluid is provided to the probe mixing chambers of the first, second, third, and fourth probes without first passing through the duct, the calibration fluid provided at a pressure sufficient to prevent fluid from the duct from entering the first, second, third, and fourth probes, the calibration fluid comprising known levels of the predetermined compounds.

6. The simultaneous multipoint testing system of claim 5, further comprising a vacuum pump in fluid communication with the global mixing chamber and the first, second, third, and fourth probes, the vacuum pump configured to induce a negative pressure within the first, second, third, and fourth probes and the global mixing chamber with respect to the duct so that fluid samples are pulled from the duct, through the first, second, third, and fourth probes, and through the global mixing chamber.

7. The simultaneous multipoint testing system of claim 5, wherein the flue gas is generated by an electric power generation plant.

8. The simultaneous multipoint testing system of claim 5, wherein the predetermined compounds comprise one or more nitrous oxides, carbon monoxide, and oxygen.

\* \* \* \* \*